US009418843B2

(12) United States Patent
Li et al.

(10) Patent No.: US 9,418,843 B2
(45) Date of Patent: Aug. 16, 2016

(54) METHOD FOR MANUFACTURING ORDERED NANOWIRE ARRAY OF NIO DOPED WITH PT IN SITU

(71) Applicant: Institute of Microelectronics, Chinese Academy of Sciences, Beijing (CN)

(72) Inventors: Dongmei Li, Beijing (CN); Xin Chen, Beijing (CN); Shengfa Liang, Beijing (CN); Jiebin Niu, Beijing (CN); Peiwen Zhang, Beijing (CN); Yu Liu, Beijing (CN); Xiaojing Li, Beijing (CN); Shuang Zhan, Beijing (CN); Hao Zhang, Beijing (CN); Qing Luo, Beijing (CN); Changqing Xie, Beijing (CN); Ming Liu, Beijing (CN)

(73) Assignee: Institute of Microelectronics, Chinese Academy of Sciences (CN)

( * ) Notice: Subject to any disclaimer, the term of this patent is extended or adjusted under 35 U.S.C. 154(b) by 0 days.

(21) Appl. No.: 14/760,890

(22) PCT Filed: Jan. 17, 2013

(86) PCT No.: PCT/CN2013/070609
§ 371 (c)(1),
(2) Date: Jul. 14, 2015

(87) PCT Pub. No.: WO2014/110760
PCT Pub. Date: Jul. 24, 2014

(65) Prior Publication Data
US 2015/0357191 A1    Dec. 10, 2015

(51) Int. Cl.
*H01L 21/00* (2006.01)
*H01L 21/02* (2006.01)
*H01L 21/465* (2006.01)
*G01N 33/00* (2006.01)
*B82Y 10/00* (2011.01)
*B82Y 40/00* (2011.01)

(52) U.S. Cl.
CPC ........ *H01L 21/02565* (2013.01); *G01N 33/004* (2013.01); *G01N 33/005* (2013.01); H01L21/02422 (2013.01); *H01L 21/02581* (2013.01); *H01L 21/02603* (2013.01); *H01L 21/02614* (2013.01); *H01L 21/465* (2013.01); *B82Y 10/00* (2013.01); *B82Y 40/00* (2013.01)

(58) Field of Classification Search
CPC ...... B22F 1/0025; B82Y 40/00; B82Y 10/00; H01L 21/02603
See application file for complete search history.

(56) References Cited

U.S. PATENT DOCUMENTS

| 6,831,017 | B1 * | 12/2004 | Li | B82Y 10/00 257/E21.131 |
| 8,278,653 | B2 * | 10/2012 | Sandhu | B01J 37/349 257/40 |
| 9,112,085 | B2 * | 8/2015 | Mi | H01L 31/03044 |
| 2011/0300400 | A1 * | 12/2011 | Tomita | B22F 1/0025 428/605 |

* cited by examiner

*Primary Examiner* — Zandra Smith
*Assistant Examiner* — John M Parker
(74) *Attorney, Agent, or Firm* — Schwegman, Lundberg & Woessner, P.A.

(57) ABSTRACT

The present disclosure provides a method for manufacturing ordered nanowires array of NiO doped with Pt in situ, comprising: growing a Ni layer on a high-temperature resistant and insulated substrate; applying a photoresist on the Ni layer, pattering a pattern region of the ordered nanowires array by applying electron beam etching on the photoresist, growing Ni on the pattern region of the ordered nanowires array, peeling off the photoresist by acetone and etching the surface of the Ni layer by ion beam etching so as to etch off the Ni layer grown on the surface of the substrate and to leave the Ni on the pattern region of the ordered nanowires array to form the ordered Ni nanowires array; dipping the ordered Ni nanowires array into a solution of $H_2PtCl_6$ so as to displace Pt on the Ni nanowires array by a displacement reaction; and oxidizing the Ni nanowires array attached with Pt in an oxidation oven to obtain the ordered nanowires array of NiO doped with Pt. The present invention is simple and practical and the sensitivity and reliability of the doped sensor on the gas of CO and $H_2$ are greatly improved.

10 Claims, 6 Drawing Sheets

METHOD FOR MANUFACTURING ORDERED NANOWIRE ARRAY OF NIO DOPED WITH PT IN SITU

This application is a U.S. National Phase Application of International Application No. PCT/CN2013/070609, filed on Jan. 17, 2013, entitled "METHOD FOR MANUFACTURING ORDERED NANOWIRE ARRAY OF NIO DOPED WITH PT IN SITU", which is incorporated herein by reference in their entirety.

TECHNICAL FIELD

The present disclosure relates to the sensor field, and particularly, to a method for manufacturing an ordered nanowires array of NiO doped with Pt in situ for a gas sensor.

BACKGROUND

Since it is facile for $H_2$ to be exploded in air so as to cause serious damages to human's lives and estates. Thus, it is import to detect hydrogen gas in daily life, industrial production and so on. There are electrochemical sensor, gas sensor of catalytic combustion, infrared sensor, semiconductor gas sensor and the like which can be used to detect hydrogen gas. The electrochemical sensor is disadvantageous for easy to poison. The infrared sensor is disadvantageous for its high cost and not easy to carry. The gas sensor of catalytic combustion is disadvantageous for its poor selectivity. The semiconductor gas sensor utilizes adsorption and reaction between the gas and the semiconductor sensitive material so as to changes the electronic property of the gas and detects such a change to identify and defect the concentration of the gas. The semiconductor sensor is easy to be manufactured and is in a low cost. However, most of the semiconductor gas sensors are based on semiconductor and metal oxide, generally should be operated at a higher temperature, and has a poor selectivity. Thus, it is important to utilize other techniques such as doping to improve its property.

NiO is one type of semiconductor oxide with an excellent property and has a good property which it is used to detect gases such as Co, H2 and the like. When the dimension of NiO is in range of nanometers, its sensitivity would be improved due to its ratio of surface area and volume and the operating temperature can be decreased. A reasonably doped sensitive film of NiO greatly improves sensitivity and stability of the gas sensor for the gas such as CO, H2 and the like. Especially after being doped with Pt, the sensitivity and selectivity of the sensor for $H_2$ may be greatly enhanced due to catalytic action of Pt.

Consequently, researches on sensitive wire of NiO doped with Pt make a positive effect on the researches and industrial production of the sensors.

SUMMARY

1) Technical Problem to be Solved

Thus, the main objective of the present disclosure is to provide a method for manufacturing ordered nanowires array of NiO doped with Pt in situ.

2) Technical Solution

In order to achieve the objective as mentioned above, the present invention provides a method for manufacturing ordered nanowires array of NiO doped with Pt in situ which comprises: growing a Ni layer on a high-temperature resistant and insulated substrate; applying a photoresist on the Ni layer, patterning a pattern region of the ordered nanowires array by applying electron beam etching on the photoresist, growing Ni on the pattern region of the ordered nanowires array, peeling off the photoresist by acetone and etching the surface of the Ni layer by ion beam etching so as to etch off the Ni layer grown on the surface of the substrate and to leave the Ni on the pattern region of the ordered nanowires array to form the ordered Ni nanowires array; dipping the ordered Ni nanowires array into a solution of $H_2PtCl_6$ so as to displace Pt on the Ni nanowires array by a displacement reaction; oxidizing the Ni nanowires array attached with Pt in an oxidation oven to obtain the ordered nanowires array of NiO doped with Pt.

In the technical solution as mentioned above, in the step of growing a Ni layer on a high-temperature resistant and insulated substrate, an electron beam evaporation or a magnetron sputtering may be utilized, in which the conditions for the electron beam evaporation are as follows: a vacuum of $10^{-4}\sim 10^{-6}$ Torr, a temperature of 1100-1600° C., an evaporation rate of 0.1-3 nm/s; and the conditions for the magnetron sputtering are as follows: a voltage of 400~800V, a magnetic field strength of 70~300 G, an air pressure of 1-10 mTorr, a current density of 5~60 mA/cm, a power density of 1~40 W/cm, and a maximum sputtering rate of 100 nm~1000 nm.

In the technical solution as mentioned above, in the step of growing a Ni layer on a high-temperature resistant and insulated substrate, the high-temperature resistant and insulated substrate may be $SiO_2$, Si, Al2O3 or ceramics.

In the technical solution as mentioned above, in the step of growing a Ni layer on a high-temperature resistant and insulated substrate, the thickness of the grown Ni layer ranges between 10 nm and 100 nm.

In the technical solution as mentioned above, the step of pattering a pattern region of the ordered nanowires array by applying electron beam etching on the photoresist may comprise pattern the photoresist applied on the Ni layer by applying electron beam etching to form the pattern region of the ordered nanowires array, and the condition for the electron beam etching are as follows: a power of 100 KeV, 5 lens, thickness of the Zep photoresist of 400-800 nm and a dose of 200-300.

In the technical solution as mentioned above, in the step of growing Ni on the pattern region of the ordered nanowires array, an electron beam evaporation or a magnetron sputtering may be utilized, in which the conditions for the electron beam evaporation are as follows: a vacuum of 10-4~10-6 Torr, a temperature of 1100-1600° C., an evaporation rate of 0.1-3 nm/s; and the conditions for the magnetron sputtering are as follows: a voltage of 400~800V, a magnetic field strength of 70~300 G, an air pressure of 1-10 mTorr, a current density of 5~60 mA/cm, a power density of 1~40 W/cm, and a maximum sputtering rate of 100 nm~1000 nm.

In the technical solution as mentioned above, in the step of growing Ni on the pattern region of the ordered nanowires array, the thickness of the grown Ni layer ranges between 50 nm and 5000 nm.

In the technical solution as mentioned above, in the step of etching the surface of the Ni layer by ion beam etching process, the conditions for the ion beam etching process are as follows: a voltage of the beam flow is 250V-500V, and a current of the beam flow is 400 mA-700 mA.

In the technical solution as mentioned above, in the step of dipping the ordered Ni nanowires array into a solution of $H_2PtCl_6$ so as to displace Pt on the Ni nanowires array by a displacement reaction, a mol concentration of the solution of $H_2PtCl_6$ is $10^{-5}M$-$10^{-3}$ M, and the time during which the ordered Ni nanowires array is dipped into the solution of $H_2PtCl_6$ to make the displace reaction is 30 seconds-30 minutes.

In the technical solution as mentioned above, in the step of oxidizing the Ni nanowires array attached with Pt in an oxidation oven, the oxidization temperature is 450° C.-950° C., and the oxidization period is 3 hours-12 hours.

3) Technical Effect

The method for manufacturing ordered nanowires array of NiO doped with Pt in situ provided by the present application firstly manufactures a Ni nanowires array by electron beam etching and to separate Pt nano-particles on the Ni nanowires by dipping the Ni nanowires array into a solution of $H_2PtCl_6$ and taking place a displacement reaction. Such a method directly dopes the Ni nanowires in the aqueous solution by the displacement reaction, which requires a lower reaction temperature and lower power consumption; in addition such a method may directly control the concentration of solution and reaction temperature so as to control the size and quantity of the nano-particles, and is simple and practical. An ordered NiO nanowires array doped with Pt may be obtained by such a method, and the sensitivity and reliability of the doped sensor on the gas of CO and $H_2$ are greatly improved. Furthermore, such a method is easily to be controlled.

BRIEF DESCRIPTION OF THE DRAWINGS

The present disclosure will be illustrated in detail by referencing to the accompany figures and in conjunction with the embodiments, in which:

FIG. 2-1~FIG. 2-5 are process flowchart of the method for manufacturing ordered nanowires array of NiO doped with Pt in situ according to embodiments of the present invention.

DETAILED DESCRIPTION

The present disclosure will be illustrated in detail by referencing to the accompany figures and in conjunction with the embodiments so that the objects, solutions and advantages of the present invention would be apparent.

First of all, the basic principle of a displacement reaction will be introduced. The replacement reaction is a reaction in which one elementary substance reacts with one compound to generate another one elementary substance and another compound. Herein, the metal of Ni with a stronger metal activity may replace the metal of Pt with a poor metal activity.

On the basis of the principle as mentioned above, the present invention utilizes an electron beam evaporation or magneto sputtering to grow a Ni layer with a thickness of 10 nm-100 nm on a high-temperature resistant substrate, utilizes an electron beam etching to pattern a pattern region of the ordered nanowires array constituted of photoresist, utilizes the electron beam evaporation or magneto sputtering to grow a Ni layer with a thickness of 50 nm-5000 nm on the pattern region of the ordered nanowires array to form an ordered Ni nanowires; peels off the photoresist and etches off the Ni layer with the thickness of 10 nm-100 nm grown on the substrate by ion beam etching so as to and to leave the Ni on the ordered nanowires array; dips the ordered Ni nanowires array into a solution of $H_2PtCl_6$ with a mol concentration of $10^{-5}M$-$10^{-3}M$ for a certain period so as to displace Pt on the Ni nanowires array by a displacement reaction; and finally, oxidizes the Ni nanowires array attached with Pt in an oxidation oven to obtain the ordered nanowires array of NiO doped with Pt.

Figure 1:
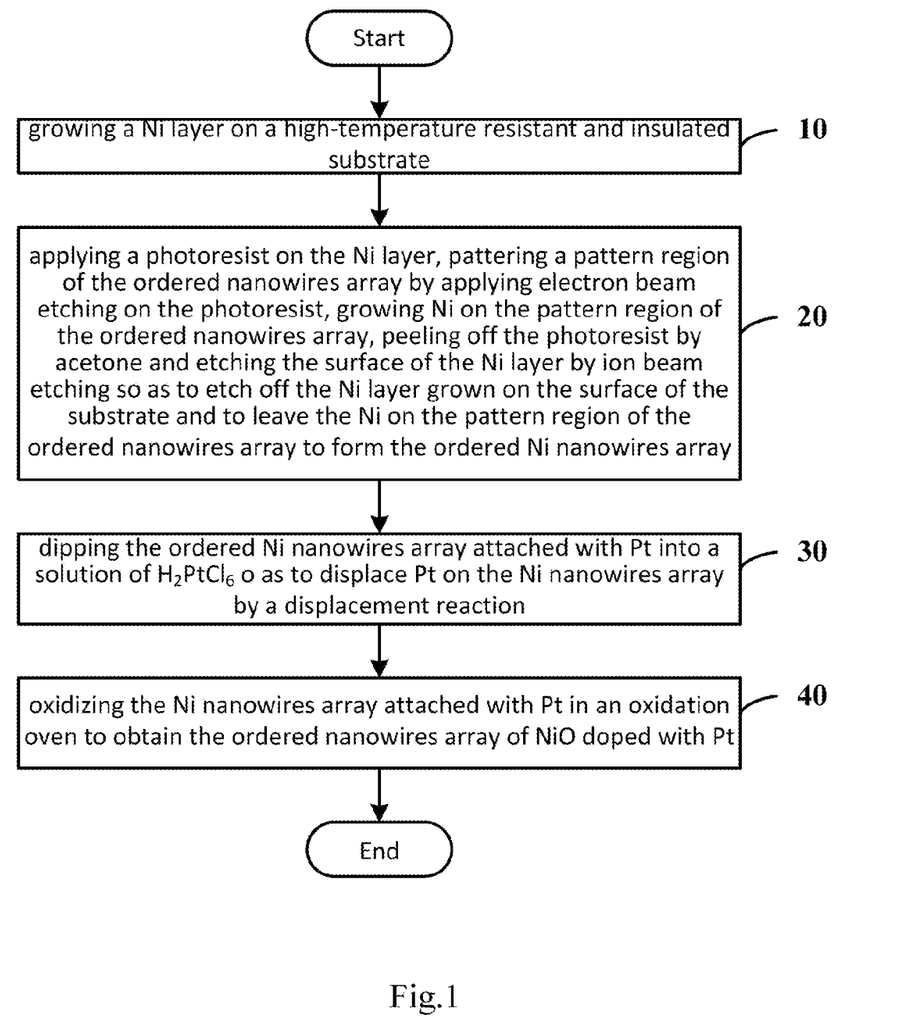
FIG. 1 is a flowchart of a method for manufacturing ordered nanowires array of NiO doped with Pt in situ according to embodiments of the present invention.

FIG. 1 shows a flowchart of a method for manufacturing ordered nanowires array of NiO doped with Pt in situ according to embodiments of the present invention. The method comprises the following steps.

At step 10, growing a Ni layer on a high-temperature resistant and insulated substrate.

In such a step, electron beam evaporation or magnetron sputtering is utilized for growing the Ni layer on the high-temperature resistant and insulated substrate. The conditions for the electron beam evaporation are as follows: a vacuum of $10^{-4}$~$10^{-6}$ Torr, a temperature of 1100-1600° C. and an evaporation rate of 0.1-3 nm/s.

In one preferred embodiment a) of the present disclosure, the conditions for the electron beam evaporation are as follows: a vacuum of $10^{-6}$ Torr, a temperature of 1300° C. and an evaporation rate of 1 nm/s; in another preferred embodiment b) of the present disclosure, the conditions for the electron beam evaporation are as follows: a vacuum of $10^{-4}$ Torr, a temperature of 1100° C. and an evaporation rate of 0.1 nm/s; in the other preferred embodiment c) of the present disclosure, the conditions for the electron beam evaporation are as follows; a vacuum of $10^{-5}$ Torr, a temperature of 1600° C. and an evaporation rate of 3 nm/s; and in one further preferred embodiment d) of the present disclosure, the conditions for the electron beam evaporation are as follows: a vacuum of $10^{-5}$ Torr, a temperature of 1400° C. and an evaporation rate of 2 nm/s.

In such a step, the conditions for the magnetron sputtering are as follows: a voltage of 400~800V, a magnetic field strength of 70~300 G, an air pressure of 1-10 mTorr, a current density of 5~60 mA/cm, a power density of 1~40 W/cm, and a maximum sputtering rate of 100 nm~1000 nm.

In one preferred embodiment a) of the present disclosure, the conditions for the magnetron sputtering are as follows: a voltage of 400V, a magnetic field strength of 100 G; an air pressure of 1 mTorr, a current density of 20 mA/cm, a power density of 20 W/cm, and a maximum sputtering rate of 100 nm/min; in another preferred embodiment b) of the present disclosure, the conditions for the magnetron sputtering are as follows: a voltage of 800V, a magnetic field strength of 300 G, an air pressure of 10 mTorr, a current density of 60 mA/cm, a power density of 40 W/cm, and a maximum sputtering rate of 1000 nm/min; in the other preferred embodiment c) of the present disclosure, the conditions for the magnetron sputtering are as follows: a voltage of 600V, a magnetic field strength of 200 G; an air pressure of 5 mTorr, a current density of 30 mA/cm, a power density of 20 W/cm, and a maximum sputtering rate of 500 nm/min; and in one further preferred embodiment d) of the present disclosure, the conditions for the magnetron sputtering are as follows: a voltage of 500V, a magnetic field strength of 160 G; an air pressure of 4 mTorr, a current density of 20 mA/cm, a power density of 15 W/cm, and a maximum sputtering rate of 360 nm/min.

The high-temperature resistant and insulated substrate generally may be $SiO_2$, Si, $Al_2O_3$, ceramics and the like. The thickness of the grown Ni layer ranges between 10 nm and 100 nm. Preferably, the thickness may be 10 nm, 20 nm, 40 nm, 60 nm, 80 nm or 100 nm.

At step 20, applying a photoresist on the Ni layer, patterning a pattern region of the ordered nanowires array by applying electron beam etching on the photoresist, growing Ni on the pattern region of the ordered nanowires array, peeling off the photoresist by acetone and etching the surface of the Ni layer by ion beam etching so as to etch off the Ni layer grown on the surface of the substrate and to leave the Ni on the pattern region of the ordered nanowires array to form the ordered Ni nanowires array.

In such a step 5, the step of patterning a pattern region of the ordered nanowires array by applying electron beam etching on the photoresist comprises pattern the photoresist applied on the Ni layer by applying electron beam etching to form the pattern region of the ordered nanowires array, and the condition for the electron beam etching are as follows: a power of 100 KeV, 5 lens, thickness of the Zep photoresist of 400-800 nm and a dose of 200-300; preferably, the conditions are as follows: a power of 100 KeV, 5 lens, thickness of the Zep photoresist of 480 nm and a dose of 260.

In the step of growing Ni on the pattern region of the ordered nanowires array, the thickness of the grown Ni layer ranges between 50 nm and 5000 nm, and an electron beam evaporation or a magnetron sputtering is utilized for growing Ni on the pattern region of the ordered nanowires array, in which the conditions for the electron beam evaporation are as follows: a vacuum of $10^{-4}$~$10^{-6}$ Torr, a temperature of 1100-1600° C., an evaporation rate of 0.1-3 nm/s. In one preferred embodiment a) of the present disclosure, the conditions for the electron beam evaporation are as follows: a vacuum of $10^{-6}$ Torr, a temperature of 1300° C. and an evaporation rate of 1 nm/s; in another preferred embodiment b) of the present disclosure, the conditions for the electron beam evaporation are as follows: a vacuum of $10^{-4}$ Torr, a temperature of 1100° C. and an evaporation rate of 0.1 nm/s; in one preferred embodiment c) of the present disclosure, the conditions for the electron beam evaporation are as follows: a vacuum of $10^{-5}$ Torr, a temperature of 1400° C. and an evaporation rate of 2 nm/s; and in one preferred embodiment d) of the present disclosure, the conditions for the electron beam evaporation are as follows: a vacuum of $10^{-6}$ Torr, a temperature of 1600° C. and an evaporation rate of 3 nm/s.

The conditions for the magnetron sputtering are as follows: a voltage of 400~800V, a magnetic field strength of 70~300 G, an air pressure of 1-10 mTorr, a current density of 5~60 mA/cm, a power density of 1~40 W/cm, and a maximum sputtering rate of 100 nm~1000 nm. In one preferred embodiment a) of the present disclosure, the conditions for the magnetron sputtering are as follows: a voltage of 400V, a magnetic field strength of 100 G, an air pressure of 1 mTorr, a current density of 20 mA/cm, a power density of 20 W/cm, and a maximum sputtering rate of 100 nm/min; in another preferred embodiment b) of the present disclosure, the conditions for the magnetron sputtering are as follows: a voltage of 800V, a magnetic field strength of 300 G, an air pressure of 10 mTorr, a current density of 60 mA/cm, a power density of 40 W/cm, and a maximum sputtering rate of 1000 nm/min; in the other preferred embodiment c) of the present disclosure, the conditions for the magnetron sputtering are as follows: a voltage of 600V, a magnetic field strength of 200 G, an air pressure of 5 mTorr, a current density of 30 mA/cm, a power density of 20 W/cm, and a maximum sputtering rate of 500 nm/min; and in one further preferred embodiment d) of the present disclosure, the conditions for the magnetron sputtering are as follows: a voltage of 200V, a magnetic field strength of 100 G, an air pressure of 3 mTorr, a current density of 15 mA/cm, a power density of 10 W/cm, and a maximum sputtering rate of 200 nm/min.

In the step of etching the surface of the Ni layer by ion beam etching process, the conditions for the ion beam etching process are as follows: a voltage of the beam flow is 250V-500V, and a current of the beam flow is 400 mA-700 mA. In one preferred embodiment a) of the present disclosure, the conditions for the ion beam etching process are as follows: a voltage of the beam flow of 300V and a current of the beam flow of 600 mA; in another preferred embodiment b) of the present disclosure, the conditions for the ion beam etching process are as follows: a voltage of the beam flow of 500V and a current of the beam flow of 700 mA; in the other preferred embodiment c) of the present disclosure, the conditions for the ion beam etching process are as follows: a voltage of the beam flow of 250V and a current of the beam flow of 400 mA; and in one further preferred embodiment c) of the present disclosure, the conditions for the ion beam etching process are as follows: a voltage of the beam flow of 400V and a current of the beam flow of 650 mA.

At step 30, dipping the ordered Ni nanowires array attached with Pt into a solution of $H_2PtCl_6$ for a certain period, e.g. 30 seconds-30 minutes, so as to displace Pt on the Ni nanowires array by a displacement reaction. Preferably, the following conditions are utilized: a mol concentration of $5*10^{-4}$M for a period of 3 minutes at 25° C.

At step 40, oxidizing the Ni nanowires array attached with Pt in an oxidation oven for a certain period to obtain the ordered nanowires array of NiO doped with Pt at an oxidation temperature of 450-950° C. for 3 hours-12 hours. Preferably, the conditions are as follows: an oxidation temperature of 550° C. for about 6 hours.

On the basis of the flowchart of a method for manufacturing ordered nanowires array of NiO doped with Pt in situ according to embodiments of the present invention as shown in FIG. 1. FIG. 2-1~FIG. 2-5 show process flowcharts of the method for manufacturing ordered nanowires array of NiO doped with Pt in situ according to embodiments of the present invention.

Figure 21:
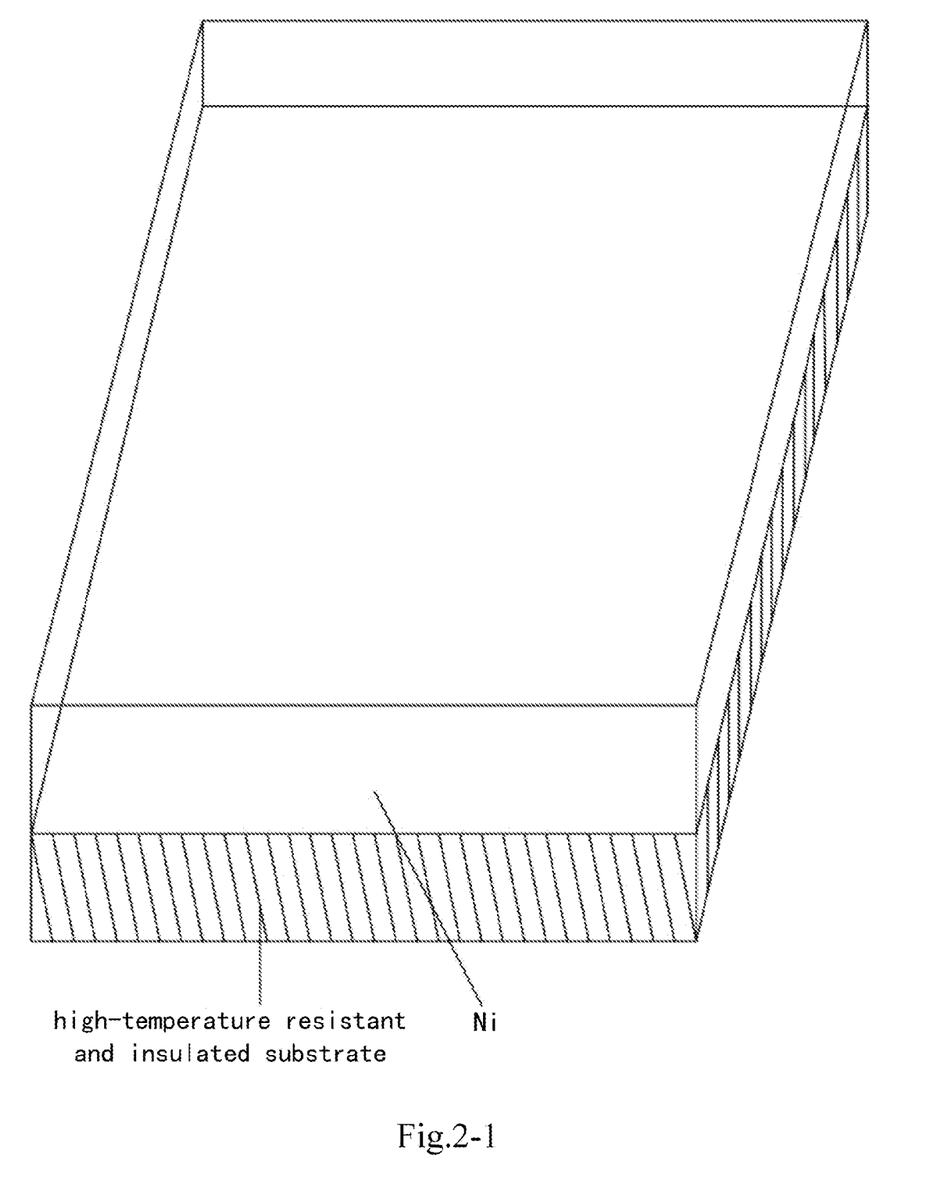

FIG. 2-1 is a schematic view after growing a Ni layer with a thickness of 10 nm on a $SiO_2$ substrate by electron beam evaporation and the condition for the electron beam evaporations are as follows: a vacuum of $10^{-6}$ Torr, a temperature of 1300° C. and an evaporation rate of 1 nm/s.

Figure 22:
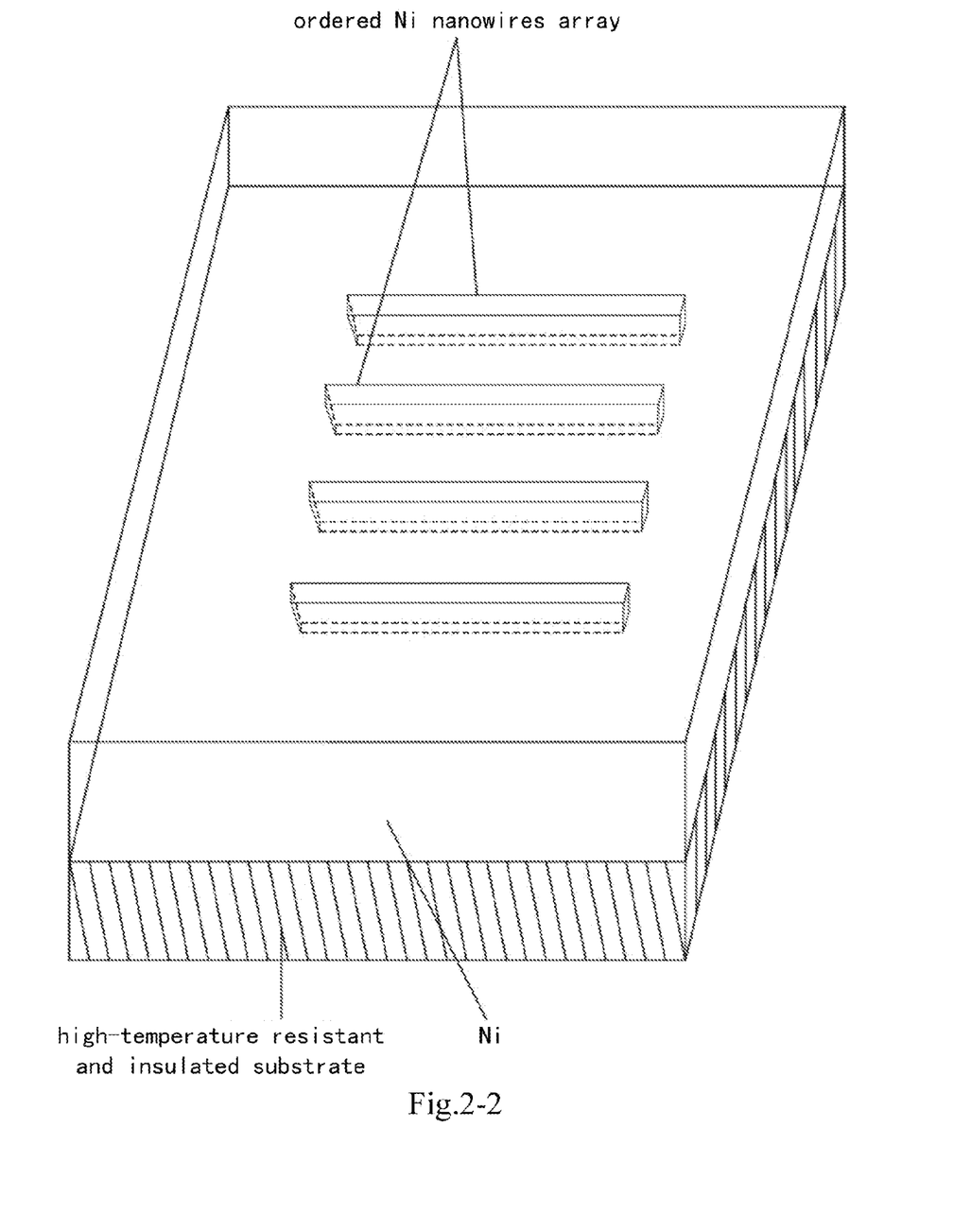

FIG. 2-2 is a schematic view after applying a photoresist on the Ni layer, patterning a pattern region of the ordered nanowires array by applying electron beam etching on the photoresist, and growing Ni with a thickness of 100 nm on the pattern region of the ordered nanowires array. The conditions for the electron beam etching are as follows: a power of 100 KeV, 5 lens, thickness of the Zep photoresist of 480 nm and a dose of 260, and the conditions for the electron beam evaporation are as follows: a vacuum of $10^{-6}$ Torr, a temperature of 1300° C. and an evaporation rate of 1 nm/s. At this moment, the thickness of the Ni layer on the pattern region of the ordered nanowires array over the substrate is 10 nm+100 nm=110 nm.

Figure 23:
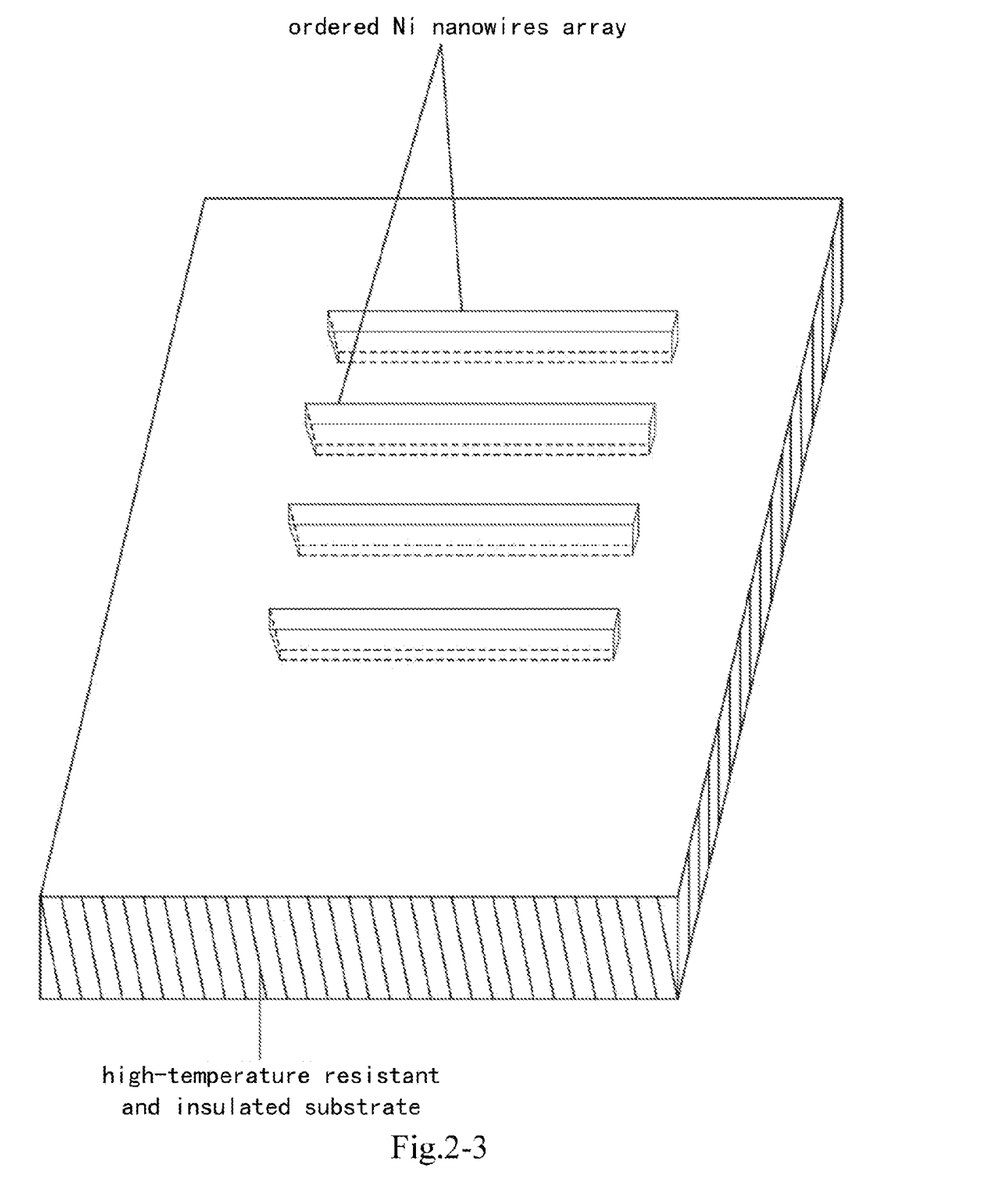

FIG. 2-3 is a schematic view after peeling off the photoresist by acetone and etching the surface of the Ni layer by ion beam etching so as to etch off the Ni layer grown on the surface of the substrate and to leave the Ni on the pattern region of the ordered nanowires array to form the ordered Ni nanowires array. After peeling off the photoresist by acetone, the thickness of the Ni layer on the pattern region of the ordered nanowires array over the substrate is 110 nm and the thickness of the Ni layer on the remaining portions is 10 nm. By etching the surface of the Ni layer by ion beam etching so as to etch off the Ni layer grown on the surface of the substrate and to leave the Ni on the pattern region of the ordered nanowires array to form the ordered Ni nanowires array, the thickness of the Ni layer are wholly etched off by 10 nm, so that the thickness of the Ni layer on the pattern region of the ordered nanowires array over the substrate is 100 nm and the Ni layer on the remaining portions are etched off. Herein, the conditions for ion beam etching are as follows: a voltage of the beam flow of 300V and a current of the beam flow of 60 mA.

Figure 24:
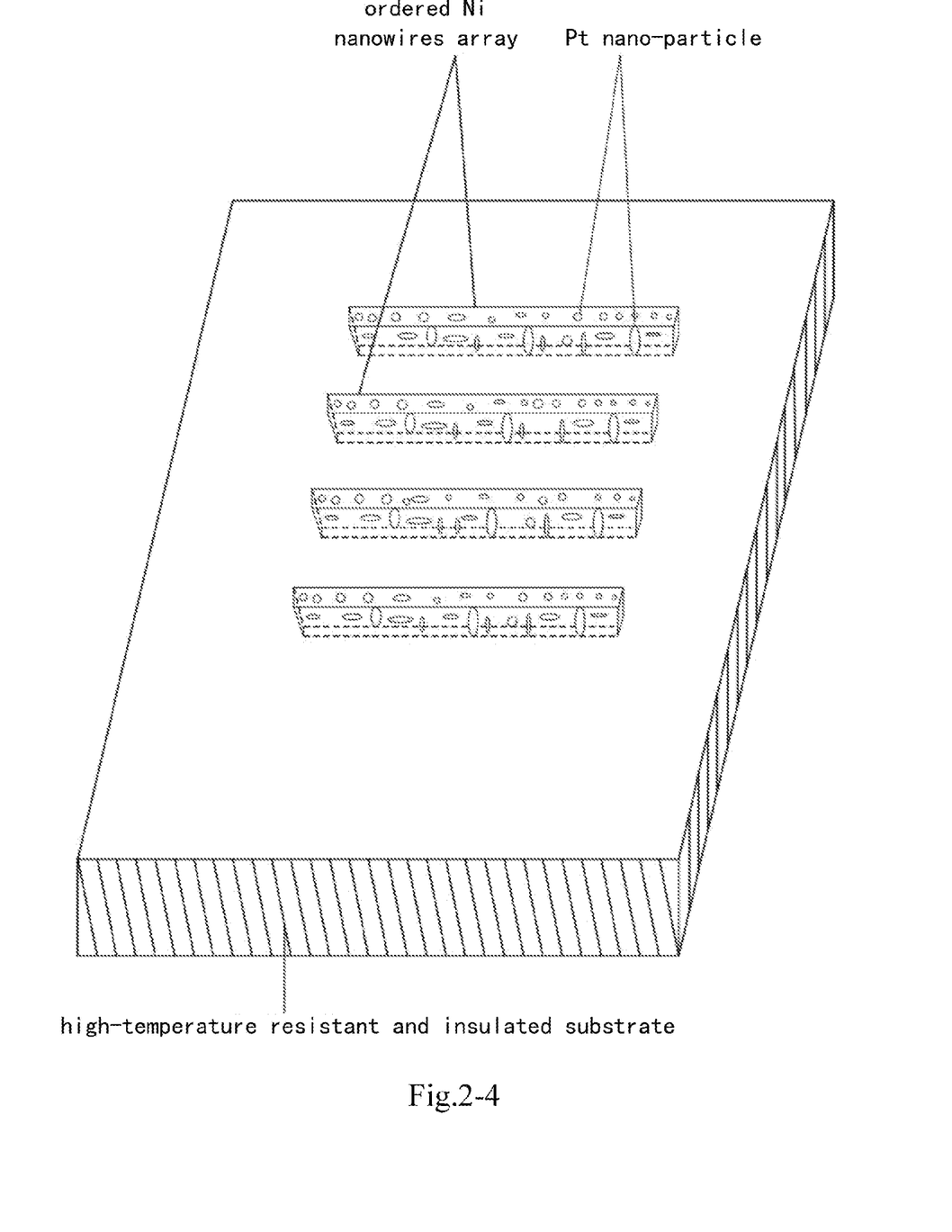

FIG. 2-4 is a schematic view after dipping the ordered Ni nanowires array into a solution of $H_2PtCl_6$ with a concentration of $5\times10^{-3}$M at a temperature of 25° C. for about 10 minutes.

Figure 25:
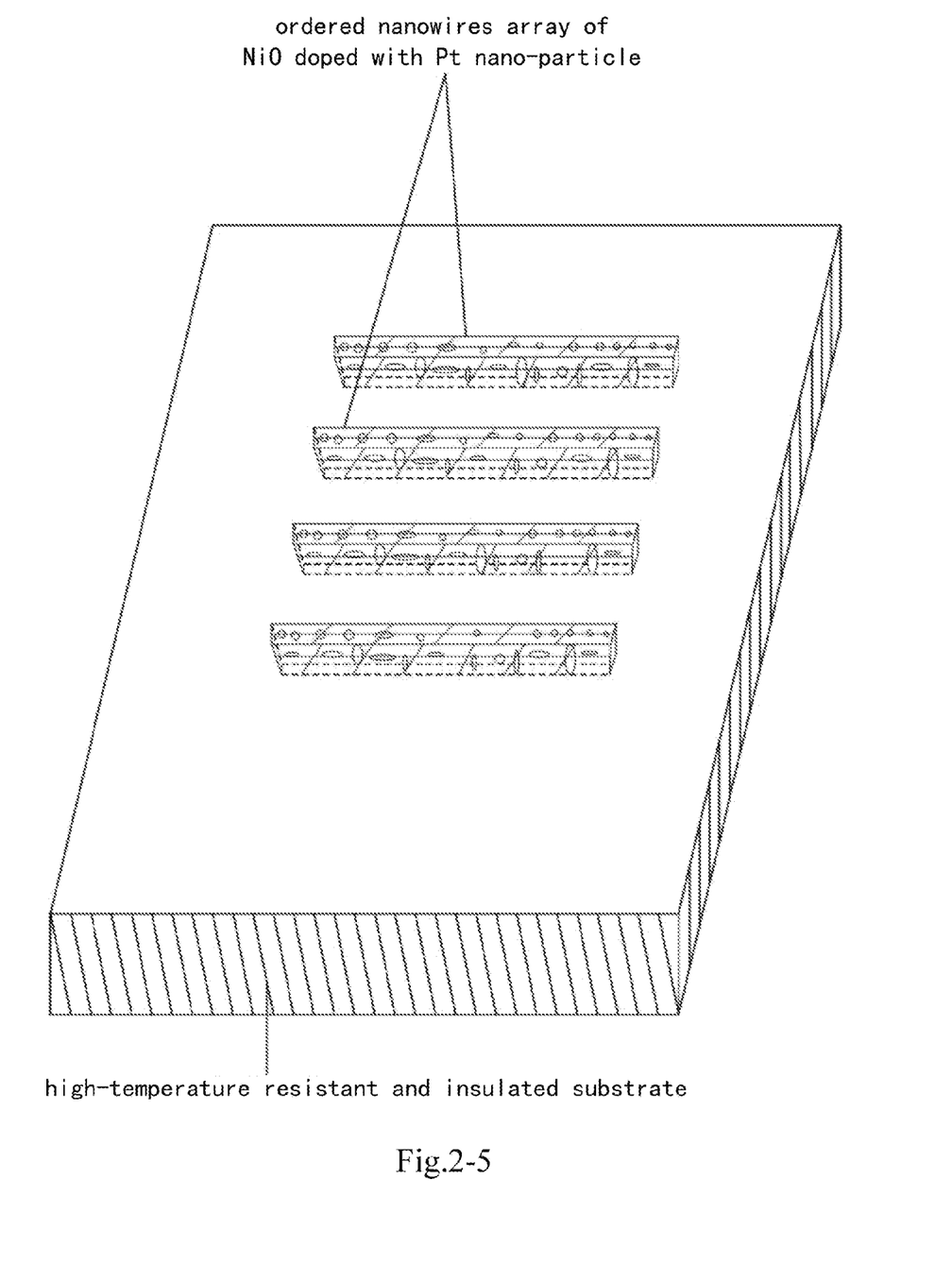

FIG. 2-5 is a schematic view after oxidizing the Ni nanowires array attached with Pt in an oxidation oven at a temperature of 550° C. for 5 hours to obtain the ordered nanowires array of NiO doped with Pt. The sensitivity and stability of doped NiO nanowires array on the gases such as CO and $H_2$ are greatly improved.

The present disclosure directly dopes the Ni nanowires in the aqueous solution by the displacement reaction, which requires a lower reaction temperature and lower power consumption; in addition such a method may directly control the concentration of solution and reaction temperature so as to control the size and quantity of the nano-particles, and is simple and practical. An ordered NiO nanowires array doped with Pt may be obtained by such a method, and the sensitivity and reliability of the doped sensor on the gas of CO and $H_2$ are greatly improved. Furthermore, such a method is easily to be controlled and utilizes a displacement reaction-thermal oxidation method to implement a controllable doping of the ordered nanowires array in situ.

The object, technical solution and advantageous effect of the present invention are further illustrated in detail by the particular embodiments as mentioned above. From the foregoing, it will be appreciated that the above mentioned embodiments are specific embodiments of the disclosure and is not intended to limit the present invention. Any modification, equivalent substitution and improvements within the scope of the spirit and principle of the present invention are included in the scope of the present invention.

We claim:

1. A method for manufacturing ordered nanowires array of NiO doped with Pt in situ, the method comprising:
   growing a Ni layer on a high-temperature resistant and insulated substrate;
   applying a photoresist on the Ni layer, patterning a pattern region of the ordered nanowires array by applying electron beam etching on the photoresist, growing Ni on the pattern region of the ordered nanowires array, peeling off the photoresist by acetone and etching the surface of the Ni layer by ion beam etching so as to etch off the Ni layer grown on the surface of the substrate and to leave the Ni on the pattern region of the ordered nanowires array to form the ordered Ni nanowires array;
   dipping the ordered Ni nanowires array into a solution of $H_2PtCl_6$ so as to displace Pt on the Ni nanowires array by a displacement reaction; and
   oxidizing the Ni nanowires array attached with Pt in an oxidation oven to obtain the ordered nanowires array of NiO doped with Pt.

2. The method according to claim 1, wherein in the step of growing a Ni layer on a high-temperature resistant and insulated substrate, an electron beam evaporation or a magnetron sputtering is utilized, in which the conditions for the electron beam evaporation are as follows: a vacuum of 10-4~10-6 Torr, a temperature of 1100-1600° C., an evaporation rate of 0.1-3 nm/s; and the conditions for the magnetron sputtering are as follows: a voltage of 400~800V, a magnetic field strength of 70~300 G, an air pressure of 1-10 mTorr, a current density of 5~60 mA/cm, a power density of 1~40 W/cm, and a maximum sputtering rate of 100 nm~1000 nm.

3. The method according to claim 1, wherein in the step of growing a Ni layer on a high-temperature resistant and insulated substrate, the high-temperature resistant and insulated substrate is $SiO_2$, Si, $Al_2O_3$ or ceramics.

4. The method according to claim 1, wherein in the step of growing a Ni layer on a high-temperature resistant and insulated substrate, the thickness of the grown Ni layer ranges between 10 nm and 100 nm.

5. The method according to claim 1, wherein in the step of patterning a pattern region of the ordered nanowires array by applying electron beam etching on the photoresist comprises pattern the photoresist applied on the Ni layer by applying electron beam etching to form the pattern region of the ordered nanowires array, and the condition for the electron beam etching are as follows: a power of 100 KeV, 5 lens, thickness of the Zep photoresist of 400-800 nm and a dose of 200-300.

6. The method according to claim 1, wherein in the step of growing Ni on the pattern region of the ordered nanowires array, an electron beam evaporation or a magnetron sputtering is utilized, in which the conditions for the electron beam evaporation are as follows: a vacuum of $10^{-4}$~$10^{-6}$ Torr, a temperature of 1100-1600° C., an evaporation rate of 0.1-3 nm/s; and the conditions for the magnetron sputtering are as follows: a voltage of 400~800V, a magnetic field strength of 70~300 G, an air pressure of 1-10 mTorr, a current density of 5~60 mA/cm, a power density of 1~40 W/cm, and a maximum sputtering rate of 100 nm~1000 nm/min.

7. The method according to claim 1, wherein in the step of growing Ni on the pattern region of the ordered nanowires array, the thickness of the grown Ni layer ranges between 50 nm and 5000 nm.

8. The method according to claim 1, wherein in the step of etching the surface of the Ni layer by ion beam etching process, the conditions for the ion beam etching process are as follows: a voltage of the beam flow is 250V-500V, and a current of the beam flow is 400 mA-700 mA.

9. The method according to claim 1, wherein in the step of dipping the ordered Ni nanowires array into a solution of $H_2PtCl_6$ so as to displace Pt on the Ni nanowires array by a displacement reaction, a mol concentration of the solution of $H_2PtCl_6$ is $10^{-5}$M-$10^{-3}$ M, and the time during which the ordered Ni nanowires array is dipped into the solution of $H_2PtCl_6$ to make the displace reaction is 30 seconds-30 minutes.

10. The method according to claim 1, wherein in the step of oxidizing the Ni nanowires array attached with Pt in an oxidation oven, the oxidization temperature is 450° C.-950° C., and the oxidization period is 3 hours-12 hours.

* * * * *